United States Patent

Weston et al.

[11] 4,053,518
[45] Oct. 11, 1977

[54] PROCESS FOR TRIS(ARALKYL)PHOSPHINES

[75] Inventors: Norma Ann Weston; Ray Leonard Hillard, both of Annandale, N.J.

[73] Assignee: American Cyanamid Company, Stamford, Conn.

[21] Appl. No.: 705,314

[22] Filed: July 14, 1976

[51] Int. Cl.² ............................ C07F 9/50; C07F 9/54
[52] U.S. Cl. ...................... 260/606.5 P; 260/606.5 F
[58] Field of Search ................... 260/606.5 P, 606.5 F

[56] References Cited

U.S. PATENT DOCUMENTS

| | | | |
|---|---|---|---|
| 2,937,207 | 5/1960 | Reuter et al. | 260/606.5 P |
| 3,257,460 | 6/1966 | Gordon et al. | 260/606.5 P |
| 3,745,191 | 7/1973 | Daigle et al. | 260/606.5 P |
| 3,746,758 | 7/1973 | Spivack | 260/606.5 P |
| 3,790,639 | 2/1974 | Daigle et al. | 260/606.5 P |

OTHER PUBLICATIONS

Kosolapoff, Organic Phosphorus Compounds, Wiley--Interscience, N. U. V., p. 52, (1972).

*Primary Examiner*—Helen M. S. Sneed
*Attorney, Agent, or Firm*—Gordon L. Hart

[57] ABSTRACT

In a solution that is free of bases and free of oxygen and which contains at least four molar proportions of the reactant tris(hydroxymethyl)phosphine for every three molar proportions of an aralkyl halide reactant, the following reaction produces tris(aralkyl)phosphine product:

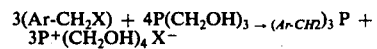

$$3(\text{Ar-CH}_2\text{X}) + 4\text{P(CH}_2\text{OH)}_3 \rightarrow (\text{Ar-CH}_2)_3\text{P} + 3\text{P}^+(\text{CH}_2\text{OH})_4 \text{X}^-$$

After separation of the phosphine product, the phosphonium salt by-products can be converted to tris(hydroxymethyl)phosphine by the addition of a base.

11 Claims, No Drawings

PROCESS FOR TRIS(ARALKYL)PHOSPHINES

This invention relates to a novel method for the preparation of tris (aralkyl) phosphines and, more particularly, to the preparation of tris (aralkyl) phosphines by reaction of an aralkyl halide with tris (hydroxymethyl) phosphine (THP).

Certain tris (aralkyl) phosphines, when converted to the corresponding phosphine oxides, are either flame retardants per se or are intermediates in the synthesis of flame retardants for plastic substrates. Heretofore, tris (aralkyl) phosphines have been prepared using a Grignard reaction, first forming the aralkyl magnesium halide, followed by reaction with phosphorus trichloride. Thus, Hinton et al, J. Chem. Soc. 1959, page 2840, reacted benzyl chloride with magnesium metal in ether to form benzyl magnesium chloride, followed by reaction thereof with phosphorous trichloride to form tris (benzyl) phosphine:

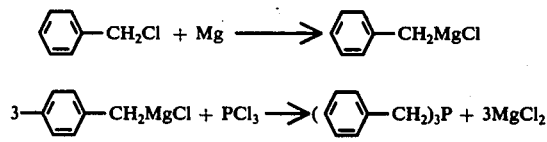

Similar reactions are described by Bailey et al, J. Am. Chem. Soc. 79, 3568 (1957) and Sander, Chem. Berichte 93, 1228 (1960).

Tris(benzyl)phosphine was also prepared by reaction of benzyl sodium with phosphorus trichloride; see Advances in Chem. Series 23, 68 (1959).

Reuter et al disclosed in their U.S. Pat. No. 2,937,207 that when one reacts tris(hydroxymethyl) phosphine with an equimolar quantity of either an alkyl halide or aralkyl halide, in the absence of a base, a quaternary phosphonium halide results, in which three hydroxymethyl groups are bound to the phosphorus atom:

where R represents the alkyl or aralkyl residue.

It would have been expected, therefore, that the reaction of an aralkyl halide with tris(hydroxymethyl) phosphine, in the absence of a base, would provide a quaternary phosphonium halide of the structure shown above.

We have now discovered a novel method which provides tris(aralkyl)phosphines in good yield comprising reacting, in an oxygen free environment and in the absence of a base, one molar proportion of an aralkyl halide with at least about 1.3 molar proportions of tris (hydroxymethyl)phosphine. This method is generally applicable to aralkyl halides of the structure: Ar—CH$_2$X, wherein AR represents a substituted or unsubstituted mono- or polycyclic aromatic nucleus and X is a halogen atom.

The process provides unexpected advantages in that 1) it provides good yields of tris(aralkyl)phosphines, 2) it produces as a by-product tetrakis(hydroxymethyl) phosphonium halides, and 3) it lends itself to continuous operation, since tetrakis(hydroxymethyl)phosphonium halide, which remains in solution on recovery of the tris (aralkyl)phosphine, is readily neutralized to tris(hydroxymethyl)phosphine, one of the starting materials in the process. The by-product formation of tetrakis(hydroxymethyl)phosphonium halide, particularly when the halide is chlorine, has the added advantage that it is a well known fire retardant compound for cotton fabrics; see Am. Dyestuff Reporter 1955, pages 1–5.

The method of the present invention is applicable to the preparation of a wide variety of tris(aralkyl) phosphines, among which are those otained by reaction of tris-(hydroxymethyl) phosphine with:

benzyl chloride (bromide, iodide)
4-methylbenzyl chloride
2-methylbenzyl chloride
2,4-dimethylbenzyl chloride
2,4,6-trimethylbenzyl chloride
1-chloromethylnaphthalene
2-chloromethylnaphthalene
4-hydroxybenzyl chloride
3,5-di.tert.butyl-4-hydroxybenzyl chloride
2,6-dimethyl-3-hydroxy-4-tert.butylbenzyl chloride and the like. While the process of the invention gives good yields of tris(aralkyl)phosphines when 1.3 to 8 molar proportions of tris(hydroxymethyl)phosphine are reacted with one molar proportion of an aralkyl halide, we prefer to react from about 2 to 4 molar proportions of tris(hydroxymethyl) phosphine per molar proportion of aralkyl halide. We believe the reaction proceeds via the equation shown below:

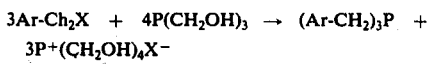

so that, stated in a different way, the reaction affords tris(aralkyl) halides in good yields when three molar proportions of an aralkyl halide are reacted with at least four molar proportions of tris(hydroxymethyl) phosphine.

The process is conducted preferably in the absence of oxygen, since the product of the reaction, depending on the nature of the aralkyl halide, may readily oxidize to the corresponding phosphine oxide. In some instances the phosphine is not so readily oxidized and if the oxide is desired it may be necessary to oxidize the phosphine by conventional procedures, for example with hydrogen peroxide. In any case, the initial product of the reaction, if care is taken to work in an oxygen-free environment, is the tris(aralkyl)phosphine.

In a preferred embodiment, a solution of tris(hydroxymethyl)phosphine is generated from an aqueous solution of a tetrakis(hydroxymethyl)phosphonium halide (for example, the chloride) by neutralization thereof with a base, such as sodium hydroxide. An aralkyl halide is then added to the solution of tris(hydroxymethyl) phosphine and the reaction mixture is heated in oxygen free environment at moderate temperatures (40°–60° C) for several hours to effect reaction. The product may then be filtered or otherwise extracted from the reaction mixture. The tetrakis(hydroxymethyl)phosphonium halide which remains in solution may then again be neutralized with a base and the reaction repeated by addition of the aralkyl halide.

The invention is illustrated in detail in the examples which follow:

EXAMPLE 1

Preparation of Tris(2,4,6-trimethylbenzyl)phosphine

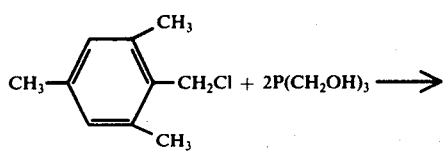

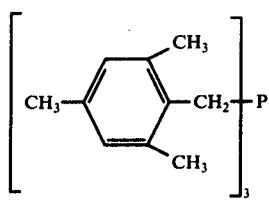

To 86 grams, 0.36 mole, of 80% tetrakis(hydroxymethyl) phosphonium chloride in 45 ml. of water, under a nitrogen atmosphere, was rapidly added 28.8 grams, 0.36 mole, of 50% sodium hydroxide solution, cooling with ice during the addition. The solution was then stirred at about 25° C for about 30 minutes. To the resulting solution containing 0.36 mole of tris(hydroxymethyl)phosphine was added 30 grams, 0.18 mole, of α-chloroisodurene and the reaction mixture heated at 45° C for about 18 hours. The mixture was then diluted with 100 ml. of water, filtered under nitrogen, the filter cake was washed with water, when with isopropanol, and dried. There was obtained 20.8 grams (80% yield) of tris(2,4,6-trimethylbenzyl)phosphine, m.p. 148°-158° C. Recrystallization from boiling isopropanol gave white needles, m.p. 157°-160° C.

EXAMPLE 2

When the procedure of Example 1 was repeated using 4 moles of tris(hydroxymethyl)phosphine per mole of α-chloroisodurene instead of 2 moles per mole thereof, tris(2,4,6-trimethylbenzyl)phosphine was obtained in 96% yield.

EXAMPLE 3

When the tris(2,4,6-trimethylbenzyl)phosphine obtained in Example 2 was recrystallized from boiling cyclohexane there was obtained tris(2,4,6-trimethylbenzyl) phosphine oxide, m.p. 232°-233° C.

This example illustrates the facile oxidation of tris(2,4,6-trimethylbenzyl)phosphine to the corresponding phosphine oxide.

EXAMPLE 4

Preparation of Tris(benzyl)phosphine

Benzyl chloride (76 grams, 0.6 mole) is added to an aqueous solution of 101 grams, 0.8 mole, of tris(hydroxymethyl) phosphine, under nitrogen, and the reaction mixture heated at 45° C for about 20 hours. The mixture is cooled to room temperature, extracted with water, filtered, washed with water, then isopropanol, and dried. Tris(benzyl) phosphine is obtained. On recrystallization from isopropanol, tris(benzyl)phosphine oxide, m.p. 208°-214° C is obtained.

This example illustrates the facile oxidation of tris(benzyl)phosphine to its corresponding phosphine oxide.

EXAMPLE 5

The procedure of Example 4 is repeated using 1-chloromethylnaphthalene instead of benzyl chloride to obtain tris(1-naphthylmethyl)phosphine.

EXAMPLE 6

The procedure of Example 4 is repeated using 3,5-di-t.butyl-4-hydroxybenzyl chloride instead of benzyl chloride to obtain tris(3,5-di-t.butyl-4-hydroxybenzyl)phosphine.

EXAMPLE 7

The procedure of Example 4 is repeated using 2,4-dimethylbenzyl chloride instead of benzyl chloride to obtain tris(2,4-dimethyl benzyl)phosphine.

In the Examples, the solvent used in water, which is the preferred solvent medium for the reaction of trishydroxymethyl phosphine with an aralkyl halide. Other solvents might be used instead of water, such as a lower alkanol or the like and a co-solvent with water might be used, for example, to solubilize a reluctant aralkyl halide reactant. The reaction temperatures used in the Examples are in the preferred range but the reaction may be carried out at any practical reaction temperature. The reaction may be carried out with the reactants either diluted or concentrated in the solvent medium, provided the relative proportions of the reactants are within the defined range.

We claim:

1. A method for the preparation of a tris(aralkyl)phosphines having the formula:

(AR—CH$_2$)$_3$P which comprises reacting, in an oxygen free environment, one molar proportion of an aralkyl halide having the formula:

AR—CH$_2$X wherein AR is a substituted or unsubstituted mono- or polycyclic aromatic nucleus and X is a halogen atom, with at least about 1.3 molar proportions of tris(hydroxymethyl)phosphine.

2. A method defined by claim 1 wherein said aralkyl halide is a substituted or unsubstituted benzyl halide.

3. A method defined by claim 1 wherein said aralkyl halide is a substituted or unsubstituted halomethyl naphthalene.

4. A method defined by claim 1 wherein the mole ratio of aralkyl halide to tris(hydroxymethyl) phosphine is in the range 1:2 to 1:4.

5. A method defined by claim 1 wherein the reactant tris(hydroxymethyl)phosphine is obtained by neutralization of an aqueous solution of a tetrakis(hydroxymethyl) phosphonium halide with a base.

6. A method defined by claim 5 wherein said tetrakis(hydroxymethyl)phosphonium halide is tetrakis(hydroxymethyl)phosphonium chloride and said base is sodium hydroxide.

7. A method for the preparation of a tris(aralkyl)phosphine represented by the formula:

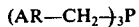

(AR—CH$_2$)$_3$P which comprises neutralizing an aqueous solution of a tetrakis(hydroxymethyl)phosphonium halide with a base, and reacting, in an oxygen free environment, the resulting solution of tris(hydroxymethyl)phosphine with an aralkyl halide, represented by the formula:

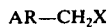

AR—CH$_2$X wherein AR is a substituted or unsubstituted mono- or polycyclic aromatic nucleus and X is a halogen atoms; the mole ratio of said aralkyl halide to said tris(hydroxymethyl)phosphine being in the range of about 1:2 to 1:4.

8. A method defined by claim 7 wherein said aralkyl halide is a substituted or unsubstituted benzyl halide.

9. A method defined by claim 7 wherein said aralkyl halide is a substituted or unsubstituted halomethylnaphthalene.

10. A method defined by claim 7 wherein said tetrakis(hydroxymethyl)phosphonium halide is tetrakis(hydroxymethyl)phosphonium chloride and said base is sodium hydroxide.

11. A method defined by claim 7 wherein the molar ratio of said aralkyl halide to said tris(hydroxymethyl)phosphine is 3:4.

* * * * *